| United States Patent [19] | [11] Patent Number: 5,061,636 |
|---|---|
| Thoraval et al. | [45] Date of Patent: Oct. 29, 1991 |

[54] CHEMICAL AGENT DETECTORS AND THEIR METHOD OF USE FOR DETECTING CHEMICAL NERVE AGENTS

[75] Inventors: Dominique Thoraval, Candiac DT; John W. Bovenkamp, Kanata, both of Canada

[73] Assignee: Her Majesty the Queen in right of Canada as represented by the Minister of National Defence, Ontario, Canada

[21] Appl. No.: 650,593

[22] Filed: Feb. 5, 1991

Related U.S. Application Data

[60] Division of Ser. No. 446,569, Dec. 5, 1989, Pat. No. 5,009,845, which is a continuation-in-part of Ser. No. 263,186, Oct. 27, 1988, abandoned.

[30] Foreign Application Priority Data

Mar. 25, 1988 [CA] Canada ................................. 562507

[51] Int. Cl.$^5$ ............................................. G01N 31/22

[52] U.S. Cl. .................................... 436/104; 436/120; 436/167; 8/506; 8/639

[58] Field of Search ............... 436/103, 104, 120, 167, 436/169; 8/506, 638, 639, 673, 687; 549/33; 546/154; 534/573, 772

[56] References Cited

U.S. PATENT DOCUMENTS

| 3,874,995 | 4/1975 | Stroterhoff | 162/181 R |
|---|---|---|---|
| 4,013,416 | 3/1977 | Rittersdorf et al. | 23/253 TP |
| 4,599,609 | 7/1986 | Blanchard | 342/602 |

*Primary Examiner*—David L. Lacey
*Assistant Examiner*—David Redding
*Attorney, Agent, or Firm*—Nixon & Vanderhye

[57] ABSTRACT

There is provided a new and useful paper type G and or type V chemical agent detector comprising a paper base including, associated with the base, at least one dye chosen from 4-((4-(phenylazo)phenyl)azo)-phenol (D.Y. 23), p-ethoxyphenyl-azo-α-hydroxynaphthoic acid (PEN), or 3', 3", 5', 5"-tetrabromophenolphthalein ethyl ester (TBPE).

7 Claims, No Drawings

CHEMICAL AGENT DETECTORS AND THEIR METHOD OF USE FOR DETECTING CHEMICAL NERVE AGENTS

This is a division of application Ser. No. 07/446,569, filed Dec. 5, 1989, now U.S. Pat. No. 5,009,845, which, in turn, is a continuation in part of Ser. No. 07/263,186, filed Oct. 27, 1988, now abandoned.

This application relates to paper chemical agent detectors.

BACKGROUND OF THE INVENTION

Paper chemical agent detectors for certain chemical warfare purposes were developed some 20 years ago and have been in widespread use by the military of many nations. In their most sophisticated form these detectors consist of a paper base in which three dyes have been incorporated, each dye being sensitive to a particular family of liquid chemical warfare agent droplets. These droplets react with the specific dyes to produce colour changes on the paper. According to the colour change produced, the type of chemical warfare agent can be identified.

Other forms of paper chemical agent detectors contain only one dye. In these cases not as much information on the type of chemical warfare agent can be obtained from the reaction with the paper detector.

A paper chemical agent detector strip is attached to the clothing or equipment of service personnel so that these personnel can immediately determine whether they or their equipment have been exposed to liquid agent contamination. Also, the paper can be used to determine if an unknown liquid on clothing, equipment, or terrain is a chemical warfare agent.

The preferred method of manufacturing these detectors is to include the dyes in the papermaking slurry so that they are integral with the paper.

As currently utilized the detectors incorporate three dyes, one each for the detection of H-type agents (mustard), G-type nerve agents and V-type nerve agents.

It has come to light that two of the three dyes heretofore incorporated in the detectors are mutagenic. That being the case, it will be very difficult or, more likely, no longer possible to utilize these two dyes. It is therefore required that new dyes be sought which meet the various criteria which are required to make the detectors.

These criteria include insolubility of the dyes in water during the papermaking process and solubility in the appropriate chemical warfare agent. The dyes must be solids with a minimum melting point which will keep them solid during a paper drying process and must give the correct strong colour on reaction with chemical warfare agent droplets. There are various other requirements including compatibility in terms of colour produced with other dyes in the detector.

The present invention provides paper chemical agent detectors incorporating dyes which meet the criteria set out above and which dyes are non-mutagenic.

PRIOR ART

The paper chemical agent detectors in widespread use heretofore incorporated three dyes as follows:

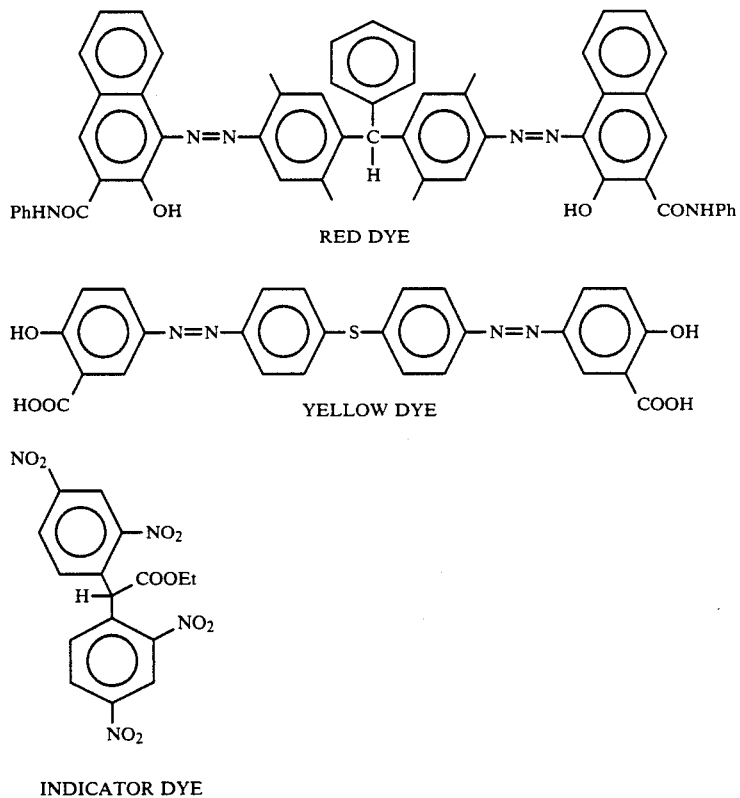

RED DYE

YELLOW DYE

INDICATOR DYE

The non-mutagenic red dye 2,5,2',5'-tetramethyltriphenylmethane-4,4'-diazo-bis-hydroxynaphthoic analide (hereinafter called Red E or simply E) continues to be usable and does not need replacement. Red E is described in the publication E. R. Nestmann et al, Carcinogenesis, Vol. 2(9), 879–883 (1981). Only the yellow dye and the indicator dye, the dyes utilized for the detection of G-type and V-type nerve agents respectively, need replacement.

BRIEF SUMMARY OF THE INVENTION

It has now been found that the various criteria which must be met by the yellow dye for use in the indicator papers are met by the following two dyes:

[Structure of D.Y.23: phenyl-N=N-phenyl-N=N-phenyl-OH]

D.Y.23

Chemical Name: 4-((4-(phenylazo)phenyl)azo)-phenol

[Structure of PEN: EtO-phenyl-N=N-naphthyl with COOH and OH groups]

PEN

Chemical Name: p-ethoxyphenyl-azo-α-hydroxynaphthoic acid.

The first of these, which is sold under the common name Disperse Yellow 23 (C.I. 26070), will hereinafter be referred to as D.Y. 23; and the second will hereinafter be designated as PEN.

A suitable replacement for the indicator dye meeting all of the necessary criteria is the following:

[Structure of TBPE: tetrabromophenolphthalein ethyl ester]

TBPE

Chemical Name: 3',3'',5',5''-tetrabromophenolphthalein ethyl ester.

This last dye is hereinafter referred to as TBPE.

DETAILED DESCRIPTION OF THE PREFERRED EMBODIMENTS

The desired dye for the detection of G-type nerve agents is a yellow dye; that is a dye which assumes a strong yellow colour when dissolved in liquid G-type nerve agents. The background colour of the paper is normally a beige, and the yellow must clearly contrast this background. Usually, especially with larger droplets, the yellow colour has an orange tinge to it. As indicated above, the dye must be insoluble in water but must be soluble in G-type nerve agents which have the general formula $$R^1-\overset{O}{\underset{F}{\overset{\|}{P}}}-OR^2$$

wherein for GD agents, $R^1$ is $CH_3$ and $R^2$ is $CH(CH_3)C(CH_3)_3$ and for GB agents, $R^1$ is $CH_3$ and $R^2$ is $CH(CH_3)_2$.

It is also highly desirable that the dye be insoluble in such liquids as petroleum products, antifreeze solutions and alcohol solutions which are likely to be encountered in battlefield conditions.

As indicated above, the dye must remain solid during any drying processes including the papermaking drying step and should therefore have a melting point greater than 100° C. It must furthermore be sufficiently stable to give the detector a good shelf life.

The dye must be non-mutagenic.

After extensive testing two dyes were found which met all of these criteria. These comprised D.Y. 23 and PEN. Having met the general criteria relating to melting point, water solubility, response to agents and compatibility with other dyes in handsheets, additional testing was undertaken to establish appropriate loading and particle size for incorporation into paper and to test sensitivity of the paper to small nerve agent droplets.

Tables I and II below set out the test results for D.Y. 23 and PEN respectively.

TABLE I

| DYE(S) | DYE LOADING (%) | BACKGROUND COLOUR | G-NERVE AGENT RESPONSE |
|---|---|---|---|
| D.Y. 23 | 0.2 | white | light yellow |
| D.Y. 23 | 0.4 | white | yellow |
| D.Y. 23 | 0.6 | off-white | yellow |
| D.Y. 23 | 0.8 | v. light brown | yellow |

In respect of D.Y. 23, the dye was ground through a No. 250 mesh screen, and handsheets were loaded with dye loadings ranging from 0.2 to 0.8 percent (dye loading is defined as parts by weight dye per 100 parts by weight dye plus dry pulp). As can be seen from Table I, handsheets with D.Y. 23 loadings as low as 0.4 to 0.6 percent gave the required yellow responses when tested with 100 to 110 micrometer droplets of GD. These results not only satisfy the criteria discussed above, but show marked improvement over the yellow dye being replaced.

TABLE II

| DYE(S) | DYE LOADING (%) | BACKGROUND COLOUR | G-NERVE AGENT RESPONSE |
|---|---|---|---|
| PEN | 0.1 | light tan | N/R |
| PEN | 0.2 | light tan | N/R |
| PEN | 0.3 | light tan | N/R |
| PEN | 0.5 | light brown | v. light yellow |
| PEN | 0.6 | light brown | v. light yellow |
| PEN | 0.8 | light brown | light yellow |
| PEN | 1.0 | light brown | light yellow |
| PEN | 1.2 | light brown | light yellow |

With respect to PEN, the dye was screened through a No. 230 mesh screen and incorporated into handsheets with loadings ranging from 0.1 to 1.2 percent. The sheets were tested with 100 to 110 micrometer droplets of liquid GD. These tests indicated that PEN gave a light yellow response at dye loadings above about 0.8 percent. Note that these were very small droplets and that much stronger yellow colours would be obtained with the larger more normal droplets.

Turning to the required replacement for the third dye, being an indicator dye, the criteria are generally the same as those in respect of the yellow dye but with some variation. The dye must change colour to a very dark green or preferably to dark blue in the presence of a base. The colour change must take place at a low enough pH for the dye to react with V-type nerve agents (which contain a substituted amine group) but this pH must be high enough to be compatible with papermaking procedures. The approximate permissible range is pH 3.5 to 8. The dye must be insoluble in water at papermaking pH levels and must be soluble in V-type nerve agents.

Other of the criteria are shared with the other dyes. It must remain solid during drying procedures, must be stable enough to provide a good shelf life to the detectors and must be non-mutagenic.

After extensive testing it was discovered that TBPE satisfied all of the above criteria. Utilizing the preferred known dye loading for the red dye and the preferred dye loadings as determined above for D.Y. 23 and PEN, handsheets were prepared to test various dye loadings of TBPE incorporated into sheets also containing red dye and either D.Y. 23 or PEN. The results of this testing are summarized in Table III.

TABLE III

| DYE(S) | DYE LOADING (%) | BACKGROUND COLOUR | VX-NERVE AGENT RESPONSE |
| --- | --- | --- | --- |
| E | 0.75 | greenish | red |
| D.Y. 23 | 0.6 | grey | yellow |
| TBPE | 1.2 | | v. dark green |
| E | 0.75 | grey | red |
| D.Y. 23 | 0.6 | | yellow |
| TBPE | 1.0 | | v. dark green |
| E | 0.75 | light | red |
| D.Y. 23 | 0.6 | grey | yellow |
| TBPE | 0.8 | | dark green |
| E | 0.75 | light | red |
| D.Y. 23 | 0.6 | grey | yellow |
| TBPE | 0.6 | | green |
| E | 0.75 | light | red |
| D.Y. 23 | 0.6 | grey | yellow |
| TBPE | 0.4 | | light green |
| E | 0.75 | light | red |
| D.Y. 23 | 0.6 | grey | yellow |
| TBPE | 0.2 | | yellow |
| E | 0.75 | light brown | red |
| PEN | 1.2 | | v. light yellow |
| TBPE | 0.8 | | green |
| E | 0.75 | brown | red |
| PEN | 1.2 | | light yellow |
| TBPE | 1.0 | | green |
| E | 0.75 | brown | red |
| PEN | 1.2 | | light yellow |
| TBPE | 1.2 | | dark green |

The results summarized in Table III indicate that the blue indicator dye TBPE is capable of detecting 100 to 110 micrometer droplets of the nerve agent VX but that the loading should preferably be at least 0.8 percent or more preferably 1.0 or 1.2 percent in order to give the required dark green response. It should be noted that TBPE actually gives a dark blue colour with VX but, since VX also disolves the yellow dye, their resultant colour response is dark green.

In respect of all three dyes, dye loadings up to about 2.0% might be utilized. Above that amount the detector becomes too expensive and in any event there is no significant improvement in detecting ability.

The paper base into which the dyes are incorporated can vary over a wide range of constituents. A preferred formulation comprises, in addition to a basic pulp formulation, agents for improvement of wet and dry strength, for pH control, for water repellency and for binding purposes. A typical formulation may contain a melamine-formaldehyde resin to improve wet and dry strength, and anionic emulsion of a sizing agent to impart water repellency, sodium aluminate for pH control and provision of aluminum ions, and alum for the provision of aluminum ions, the aluminum ions interacting with pulp fibres to bind the sizing agent to the fibres.

A typical melamine-formaldehyde resin is Parez 607 TM. A suitable sizing agent is Newphor 100 TM.

The order of addition of the additives to the pulp slurry is important and comprises in order the resin, the aluminum/sodium aluminate, the sizing agent and the dye slurries.

While the concentrations of the various additives may be varied over substantial ranges to suit particular conditions, a typical and preferred formulation comprises a pulp slurry comprising a 50:50 mixture of softwood and hardwood pulp, and containing on a parts of additive per 100 parts slurry basis Parez 607 3.0, alum 2.1, sodium aluminate 0.3 and Newphor 100 0.5. Typical particle sizes for the dyes included in the preferred paper slurry formulation are as follows. For the red dye a water slurry crushed in a roller mill at a 0.5 millimeter gap followed by filtering the slurry through a No. 200 mesh screen is suitable. A similar procedure is suitable for D.Y. 23. The TBPE and PEN are preferably passed dry through a No. 230 mesh screen and then dispersed in acidic water. Other particle sizes may be used, but if the particle size becomes too small, the paper will develop unacceptable background colour; and if the particle size becomes too large, the paper will not be capable of detecting very small droplets of chemical warfare agents.

A typical pH for the pulp formulation is about 4.2.

It will be appreciated by those skilled in the art that the detector dyes according to the invention are not novel compounds per se. For example, as indicated above, Disperse Yellow 23 is a well documented dye material. PEN is described in the publication A. C. Sircar et al, J. Soc. Chem. Ind., Vol. 31, 968 (1912) and TBPE is described in the publication M. M. Danis et al, J. Research Nat'l, Bur. Standards, Vol. 39, 221 (1947). However, the use of such materials for detecting and/or identifying chemical agents is both new and unobvious. Moreover, although it is preferred according to the invention that the detector dyes are associated with a base or substrate such as paper and various suitable fabric materials, it is contemplated that the detector dyes could also be used without such a base or substrate under the appropriate conditions as would be apparent to those skilled in the art.

We claim:

1. A method of detecting type G chemical nerve agents comprising exposing a detector material to a fluid, said material comprising at least one dye selected from the group consisting of 4-[(phenylazo)phenyl)azo]-phenol (Disperse Yellow 23), and p-ethoxyphenyl-azo-α-hydroxynaphthoic acid (PEN), and examining the detector for a predetermined color change in the detector confirming the presence of said chemical agent.

2. The method of claim 1, wherein the detector material comprises

4-[(phenylazo)phenyl)azo]-phenol (Disperse Yellow 23), whereby in the presence of a G-type chemical agent the detector material assumes a characteristic yellow color.

3. The method of claim 2, wherein the detector material is impregnated in a paper substrate.

4. The method of claim 1, wherein the detector material comprises p-ethoxyphenyl-azo-α-hydroxynaphthoic acid (PEN), whereby in the presence of a G-type chemical agent the detector material assumes a characteristic yellow color.

5. The method of claim 4, wherein the detector material is impregnated in a paper substrate.

6. A method of detecting a V-type chemical agent, comprising exposing a detector material to a fluid, said detector material comprising 3',3'',5',5''-tetrabromophenolphtalein ethyl ester (TBPE), whereby in the presence of a V-type chemical agent the detector material assumes a characteristic green color.

7. The method of claim 6, wherein the detector material is impregnated in a paper substrate.

* * * * *